US009724176B2

(12) United States Patent
Chan et al.

(10) Patent No.: US 9,724,176 B2
(45) Date of Patent: Aug. 8, 2017

(54) ALVEOLAR BONE AUGMENTATION KIT (71) Applicant: Chan Pik-Chi, Kowloon (HK)

(72) Inventors: Pik-Chi Chan, Kowloon (HK);
Weng-Kong Tam, Kowloon (HK);
Weng-Heng Tam, Kowloon (HK)

(73) Assignee: Pik Chi Chan, Kowloon (HK)

( * ) Notice: Subject to any disclaimer, the term of this patent is extended or adjusted under 35 U.S.C. 154(b) by 1162 days.

(21) Appl. No.: 13/734,481

(22) Filed: Jan. 4, 2013

(65) Prior Publication Data

US 2014/0080091 A1 Mar. 20, 2014

(30) Foreign Application Priority Data

Sep. 14, 2012 (CN) .......................... 2012 1 0344365

(51) Int. Cl.
*A61C 8/00* (2006.01)
*A61F 2/28* (2006.01)
*A61C 8/02* (2006.01)
*A61F 2/30* (2006.01)

(52) U.S. Cl.
CPC .......... *A61C 8/0089* (2013.01); *A61F 2/2846* (2013.01); *A61C 8/0006* (2013.01); *A61F 2/2803* (2013.01); *A61F 2002/3055* (2013.01); *A61F 2002/30507* (2013.01)

(58) Field of Classification Search
CPC ..... A61C 8/0089; A61C 8/0093; A61C 8/006; A61C 8/0006; A61F 2/2846; A61F 2/2803; A61F 2002/30507; A61F 2002/3055
USPC ............................. 433/173; 606/72, 73, 105
See application file for complete search history.

(56) References Cited

U.S. PATENT DOCUMENTS

| 5,769,630 A | * | 6/1998 | Hoffman | A61B 17/663 433/173 |
| 5,769,850 A | * | 6/1998 | Chin | A61B 17/171 606/102 |
| 5,885,290 A | * | 3/1999 | Guerrero | A61B 17/663 433/7 |
| 5,961,329 A | * | 10/1999 | Stucki-McCormick | A61B 17/666 433/173 |
| 5,980,252 A | * | 11/1999 | Samchukov | A61C 8/0006 433/172 |

(Continued)

FOREIGN PATENT DOCUMENTS

CN 101384227 A 3/2009
WO WO-02/060333 A1 8/2002

*Primary Examiner* — Nicholas Lucchesi
(74) *Attorney, Agent, or Firm* — Muncy, Geissler, Olds & Lowe, P.C.

(57) ABSTRACT

An alveolar bone augmentation kit includes lateral and vertical augmentation sets. The lateral augmentation set is made of a bone graft material. The lateral augmentation set can be implanted in an alveolar bone. The vertical augmentation set includes two attachment units and an adjustment and lift unit. The first attachment unit includes a post and a first fastener. The post secured to the alveolar bone by the first fastener. The adjustment and lift unit includes a beam, an elevating rod movably connected to the beam, and a joint for rotationally connecting the beam to the post. The second attachment unit includes a plate and a second fastener. A first portion of the plate is placed against the elevating rod. The second fastener is driven in the alveolar bone via an opening in a second portion of the plate and an aperture in the lateral augmentation set.

17 Claims, 5 Drawing Sheets

(56) References Cited

U.S. PATENT DOCUMENTS

| | | | | |
|---|---|---|---|---|
| 6,884,243 | B2* | 4/2005 | Sellers | A61B 17/663 606/105 |
| 6,972,020 | B1* | 12/2005 | Grayson | A61B 17/663 606/90 |
| 7,396,232 | B2* | 7/2008 | Fromovich | A61B 90/02 433/173 |
| 7,588,579 | B2* | 9/2009 | Mommaerts | A61B 17/663 606/105 |
| 8,226,655 | B1* | 7/2012 | Sixto, Jr. | A61C 8/0006 606/58 |
| 9,095,377 | B2* | 8/2015 | Karlsson | A61B 17/666 |
| 2003/0055433 | A1* | 3/2003 | Krenkel | A61C 8/0006 606/86 R |
| 2003/0105463 | A1* | 6/2003 | Wolgen | A61B 17/663 606/71 |
| 2004/0152046 | A1* | 8/2004 | Minoretti | A61B 17/663 433/173 |
| 2008/0081315 | A1 | 4/2008 | Kim et al. | |
| 2009/0117519 | A1* | 5/2009 | Freilich | A61B 17/68 433/173 |
| 2009/0220914 | A1 | 9/2009 | Gershenzon | |
| 2012/0094254 | A1* | 4/2012 | Uchitel | A61C 8/0018 433/173 |
| 2013/0196288 | A1* | 8/2013 | Schleier | A61C 8/0006 433/173 |

* cited by examiner

ALVEOLAR BONE AUGMENTATION KIT

BACKGROUND OF INVENTION

1. Field of Invention

The present invention relates to alveolar bone augmentation and, more particularly, to a kit for laterally and vertical augmenting an alveolar bone.

2. Related Prior Art

In dental implantation, an implant fixture made of metal such as titanium is implanted in an alveolar bone. A prosthetic crown is connected to the implant fixture that is expected to be firmly held by the alveolar bone three to six months after the implantation. For aesthetics, comfort and functionality, dental implantation is getting popular in comparison with dental bridge prosthesis and removable denture placement.

The foundation of successful dental implantation is a healthy alveolar bone that provides firm support for an implant fixture. The dental implantation is not recommended in cases of alveolar atrophy or alveolar deficiency. To solve this problem, the atrophic or deficient alveolar bone must be augmented so that it can be strong enough to provide firm support for the implant fixture.

The present invention is therefore intended to obviate or at least alleviate the problems encountered in prior art.

SUMMARY OF INVENTION

It is the primary objective of the present invention to provide an alveolar bone augmentation kit.

To achieve the foregoing objective, the alveolar bone augmentation kit includes lateral and vertical augmentation sets. The lateral augmentation set is made of a bone graft material. The lateral augmentation set can be implanted in an alveolar bone. The vertical augmentation set includes two attachment units and an adjustment and lift unit. The first attachment unit includes a post and a first fastener. The post is connected to the alveolar bone by the first fastener. The adjustment and lift unit includes a beam, an elevating rod movably connected to the beam, and a joint for rotationally connecting the beam to the post. The second attachment unit includes a plate and a second fastener. A first portion of the plate is placed against the elevating rod. The second fastener is driven in the alveolar bone via an opening in a second portion of the plate and an aperture in the lateral augmentation set.

Other objectives, advantages and features of the present invention will be apparent from the following description referring to the attached drawings.

BRIEF DESCRIPTION OF DRAWINGS

The present invention will be described via detailed illustration of the preferred embodiment referring to the drawings wherein.

DETAILED DESCRIPTION OF PREFERRED EMBODIMENT

Figure 1:
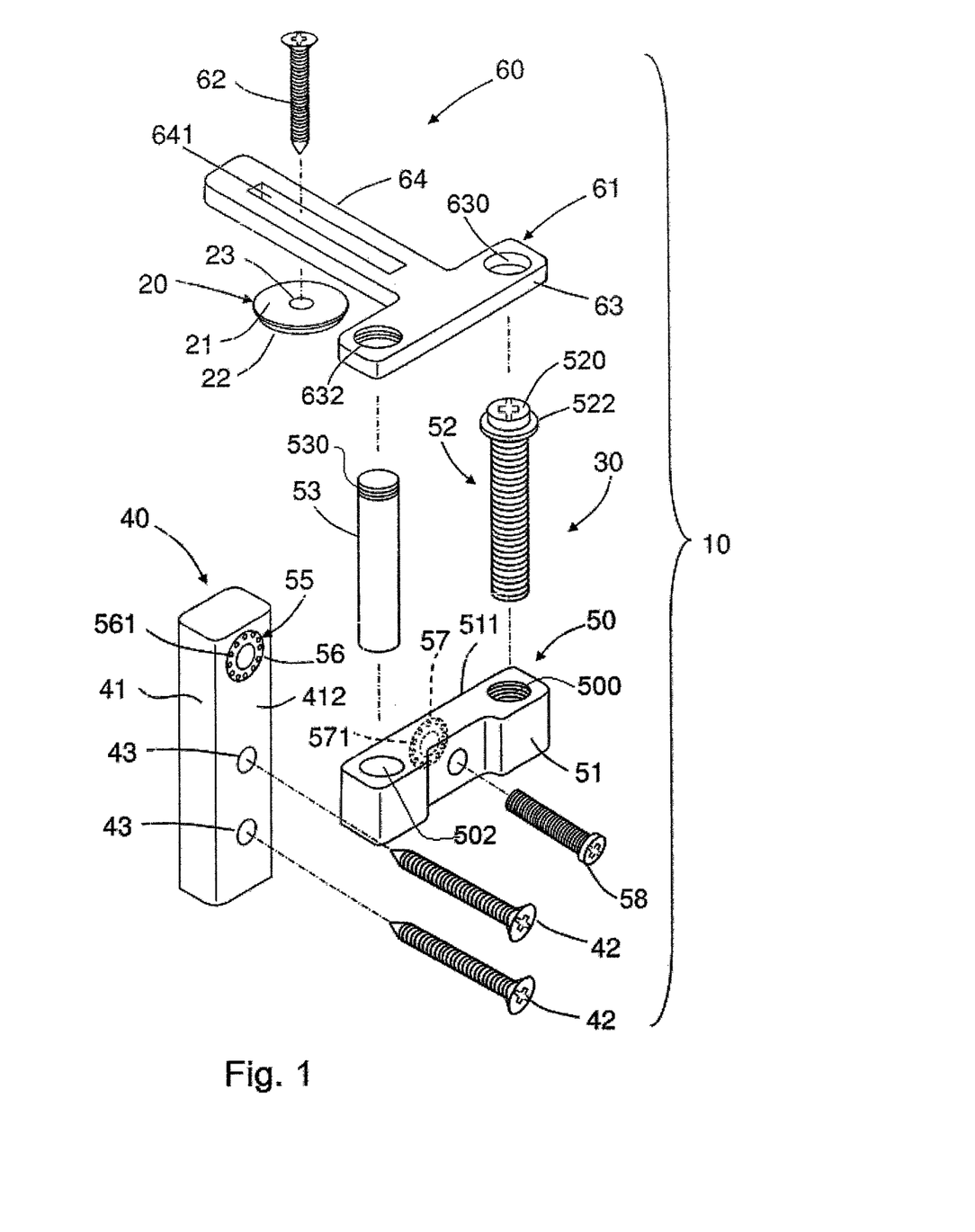
FIG. 1 is an exploded view of an alveolar bone augmentation kit according to the preferred embodiment of the present invention.
Figure 2:
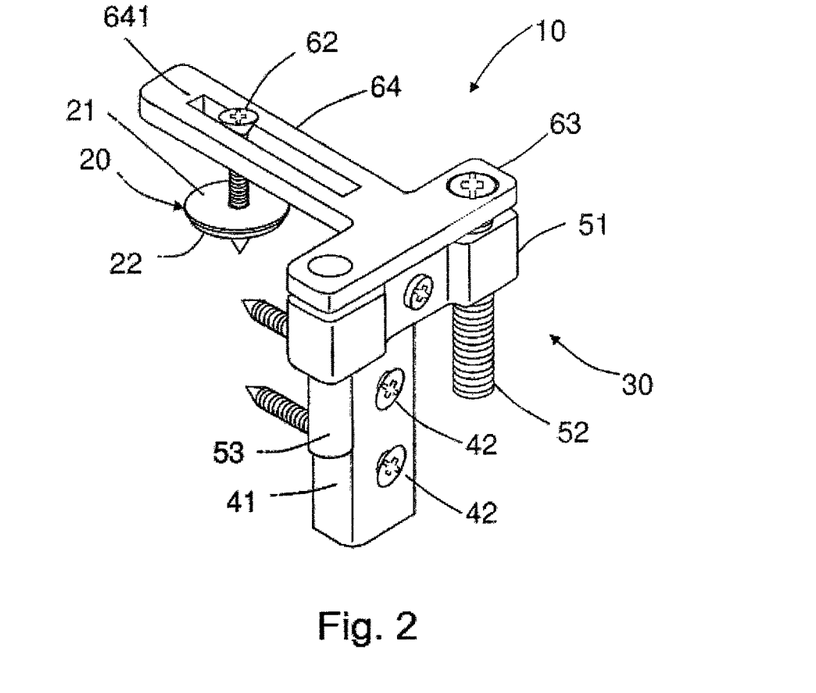
FIG. 2 is a perspective view of the alveolar bone augmentation kit shown in FIG. 1.

Referring to FIGS. 1 and 2, there is shown an alveolar bone augmentation kit 10 according to the preferred embodiment of the present invention. The alveolar bone augmentation kit 10 includes a lateral augmentation set 20 and a vertical augmentation set 30.

The lateral augmentation set 20 includes two rings 21 and 22 coaxially connected to each other. The first ring 21 includes an external diameter larger than that of the second ring 22. An aperture 23 is defined in the rings 21 and 22. The profile of each of the rings 21 and 22 may be circular or in any other proper shape.

The first ring 21 may be made of a resorbable material such as a tissue membrane and a collagen membrane. The first ring 21 may alternatively be made of a non-resorbable material such as a polytetrafluoroethylene membrane. The first ring 21 may alternatively be made of a mixture of a resorbable material with a non-resorbable material.

The second ring 22 is made of a resorbable, biodegradable, osteo-conductive and/or osteo-inductive material. Such materials include but are not limited to hydroxyapatite ("HA"), tricalcium phosphate ("TCP"), calcium sulphate, biphasic calcium phosphate ("BCP") and biocompatible ceramics.

The vertical augmentation set 30 is made of at least one sort of metal that can be implanted in human bodies. The vertical augmentation set 30 includes a first attachment unit 40, an adjustment and lift unit 50 and a second attachment unit 60.

The first attachment unit 40 includes a post 41 and at least one fastener 42 such as a bone screw extending through the post 41. Preferably, the first attachment unit 40 includes two fasteners 42. The post 41 is an elongated flat element. The fasteners 42 are arranged along a vertical axis of the post 41 or in any other proper manner. The axes of the fasteners 42 may be perpendicular to a lateral face of the post 41. The axes of the fasteners 42 may alternatively extend at any other proper angle with respect to the lateral face of the post 41. The post 41 includes at least one opening 43. Preferably, the post 41 includes two openings 43 through which the fasteners 42 extend. The openings 43 can be apertures or slots.

The adjustment and lift unit 50 includes a beam 51, an elevating rod 52, a guiding rod 53 and a joint 55. The beam 51 includes a screw hole 500 defined therein and an aperture 502 defined therein.

The elevating rod 52 includes a head 520 formed at an end and an annular flange 522 formed next to the head 520. The head 520 may include a cruciform recess for receiving a cruciform tip of a screwdriver. The head 520 may alternatively include a groove for receiving a flat tip of a screwdriver. The elevating rod 52 is driven into the screw hole 500. Thus, the elevating rod 52 is perpendicularly movably connected to the beam 51.

The guiding rod 53 includes a thread 530 formed thereon near an end. The guiding rod 53 is movably inserted in the aperture 502. Thus, the guiding rod 53 is perpendicular to the beam 51. Hence, the guiding rod 53 is parallel to the elevating rod 52.

The joint 55 includes two contact faces 56 and 57 and a fastener 58. The contact face 56 is formed on an external side 412 of the post 41. The contact face 57 is formed on an internal side 511 of the beam 51. The contact face 56 includes angle-retaining elements 561 corresponding to angle-retaining elements 571 formed on the contact face 57. For example, the angle-retaining elements 561 may be bosses while the angle-retaining elements 571 are recesses to receive the bosses. The angle-retaining elements 561 may alternatively be recesses while the angle-retaining elements 571 are bosses for insertion in the recesses.

The fastener 58 is preferably a threaded bolt. The fastener 58 is driven into a screw hole centrally defined in the contact face 57 through an aperture centrally defined in the contact face 56. Thus, the beam 51 is rotationally connected to the post 41.

The contact face 56 is in contact with the contact face 57 when the post 41 is pivotally connected to the beam 51 by the fastener 58. The beam 51 is kept in a selected one of angles relative to the post 41 as the angle-retaining elements 561 are engaged with the angle-retaining elements 571. The angle-retaining elements 561 and 571 may be in any other proper configuration than the boss-and-recess configuration.

The second attachment unit 60 includes a plate 61 and a fastener 62 such as a bone screw. The plate 61 is a T-shaped element formed with a first portion 63 and a second portion 64. The first portion 63 of the plate 61 includes an aperture 630 and screw hole 632 defined therein. The second portion 64 of the plate 61 includes an opening 641 defined therein. The opening 641 may be an aperture or a slot.

The head 520 is inserted in the aperture 630 while the annular flange 522 is placed against the first portion 63 of the plate 61. The thread 530 is driven in the screw hole 632. Thus, the guiding rod 53 is secured to the first portion 63 of the plate 61. The plate 61 is movable up and down by rotating the elevating rod 52 on the beam 51. The movement of the plate 61 is rendered smooth by the guiding rod 53 that is synchronously movable up and down relative to the beam 51.

The fastener 62 is inserted through the opening 641. The fastener 62 is then driven in the aperture 23 of the lateral augmentation set 20.

Figure 3:
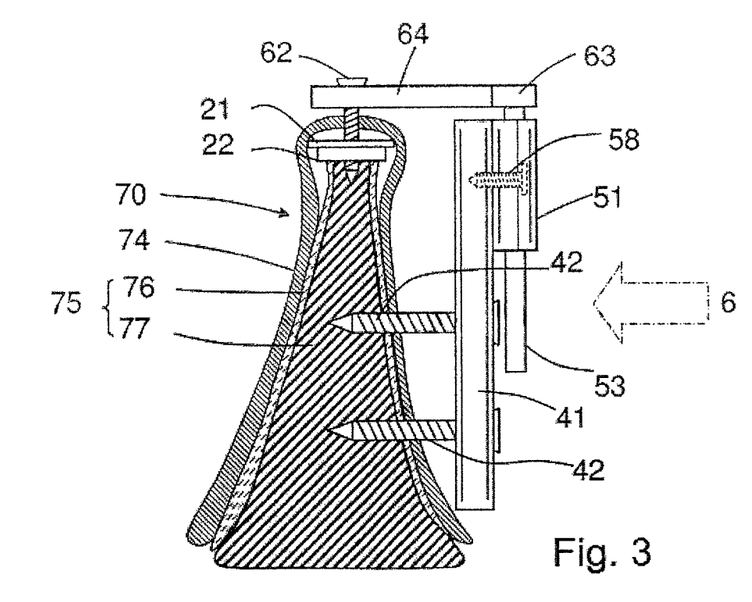
FIG. 3 is a cross-sectional view of an alveolar bone and the alveolar bone augmentation kit shown in FIG. 2.

Referring to FIG. 3, implantation of the alveolar bone augmentation kit 10 in a periodontal structure 70 will be described. The periodontal structure 70 includes a gingiva 74 and an alveolar bone 75. The alveolar bone 75 includes a cortex 76 and marrow 77. As shown in FIG. 3, the periodontal structure 70 is atrophic, deficient and unhealthy. The alveolar bone augmentation kit 10 is used to laterally and vertically augment the periodontal structure 70.

The lateral augmentation set 20 is implanted into the alveolar bone 75 via the gingiva 74. The post 41 is placed on the buccal, palatal or lingual side of the periodontal structure 70. The fastener 42 is driven into the alveolar bone 75 through the post 41, thus securing the post 41 to the buccal, palatal or lingual side of the alveolar bone 75. The beam 51 is connected to the post 41 via the fastener 58. The contact faces 56 and 57 are used to adjust the angle of the beam 51 relative to the post 41. The post 41 is secured to a portion of the alveolar bone 75 by the fastener 42 based on the condition of the alveolar bone 75. Hence, the post 41 may not be perfectly vertical. However, the plate 61 must be as close to horizontal as possible, and the elevating rod 52 and the guiding rod 53 must be vertical to render the plate 61 horizontal. Thus, the vertical augmentation of the alveolar bone 75 will not be biased. To this end, the angle of the beam 51 relative to the post 41 is adjustable. The angle-retaining elements 561 and 571 of the contact faces 56 and 57 are used to keep the beam 51 in a desired angle relative to the post 41.

The plate 61 is placed horizontally on the periodontal structure 70. The first portion 63 of the plate 61 is placed on the elevating rod 52 and the guiding rod 53. The fastener 62 is driven into a distracted bone fragment 751 of the alveolar bone 75 through the aperture 23 of the lateral augmentation set 20 and the opening 641 of the second portion 64. The distracted bone fragment 751 is formed by bone decortication or corticotomy of the alveolar bone 75. The bone decortication and corticotomy of the alveolar bone 75 are well-known surgical procedures. In brief, the cortex 76 of the alveolar bone 75 is cut in an annular manner while the marrow 77 is not completely cut and separated. Hence, the separated cortex 76 and a portion of the marrow 77 together form the distracted bone fragment 751. The distracted bone fragment 751 obtains an excellent blood supply from the marrow 77, thus considerably reducing the risks of necrosis of the distracted bone fragment 751 during distraction.

Figure 4:
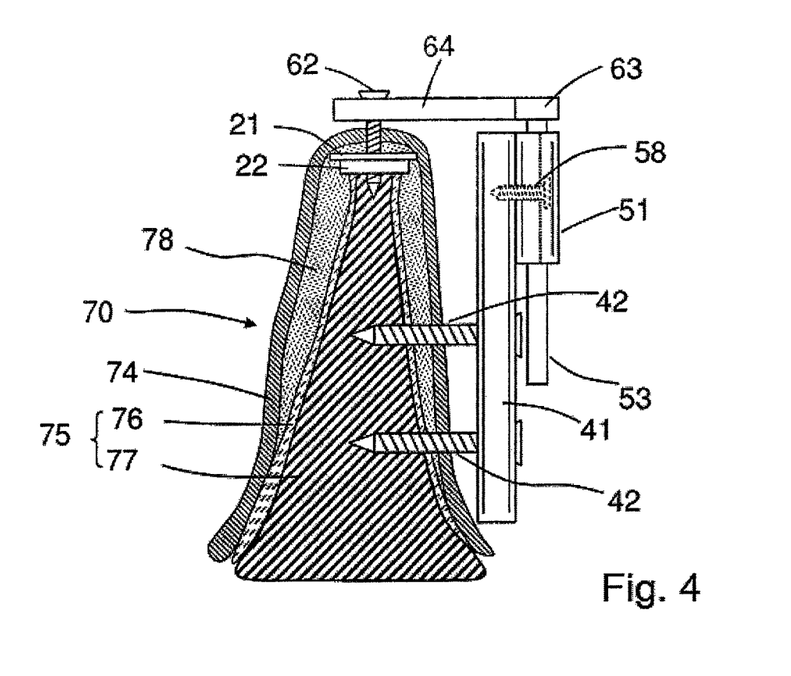
FIG. 4 is a cross-sectional view of the alveolar bone laterally augmented by the alveolar bone augmentation kit shown in FIG. 3.

Referring to FIG. 4, the lateral augmentation of the alveolar bone 75 by the alveolar bone augmentation kit 10 will be described. The second ring 22 of the lateral augmentation set 20 is made of at least one bone graft material that can be mineralized to grow a new bone 78 around the alveolar bone 75.

The functions of the first ring 21 of the lateral augmentation set 20 will be described. Firstly, the first ring 21 prevents soft tissues from growing into the bone graft material during the augmentation of the alveolar bone 75. The soft tissues would otherwise occupy space in the new bone 78 and disturb the mineralization of the bone graft material. Secondly, the first ring 21 avoids bacterial contamination of the second ring 22 and the underlying materials via the leakage of wound closure. Thirdly, the first ring 21 expands the gingiva 74 to provide space for the mineralization of the bone graft material. In addition, the first ring 21 prevents the gingiva 74 from contracting and hence suppressing the second ring 22 during augmentation.

If the first ring 21 is made of a resorbable material, resorption time of the first ring 21 should be long enough for fulfillment of the above-mentioned functions. The first ring 21 should be completely resorbed after the completion of the mineralization of the bone graft material. If the first ring 21 is resorbed too soon, the functions will not be fulfilled.

If the first ring 21 is made of a non-resorbable material, the first ring 21 fulfills the functions during the entire augmentation of the alveolar bone 75 without any risk of early resorption. The first ring 21 is removed from the periodontal structure 70 after the augmentation of the alveolar bone 75 is completed.

The lateral augmentation set 20 expands the width of the space defined between the gingiva 74 and the alveolar bone 75 to allow the growth of the new bone 78 via the mineralization of the bone graft material in the space, i.e., the lateral augmentation.

Figure 5:
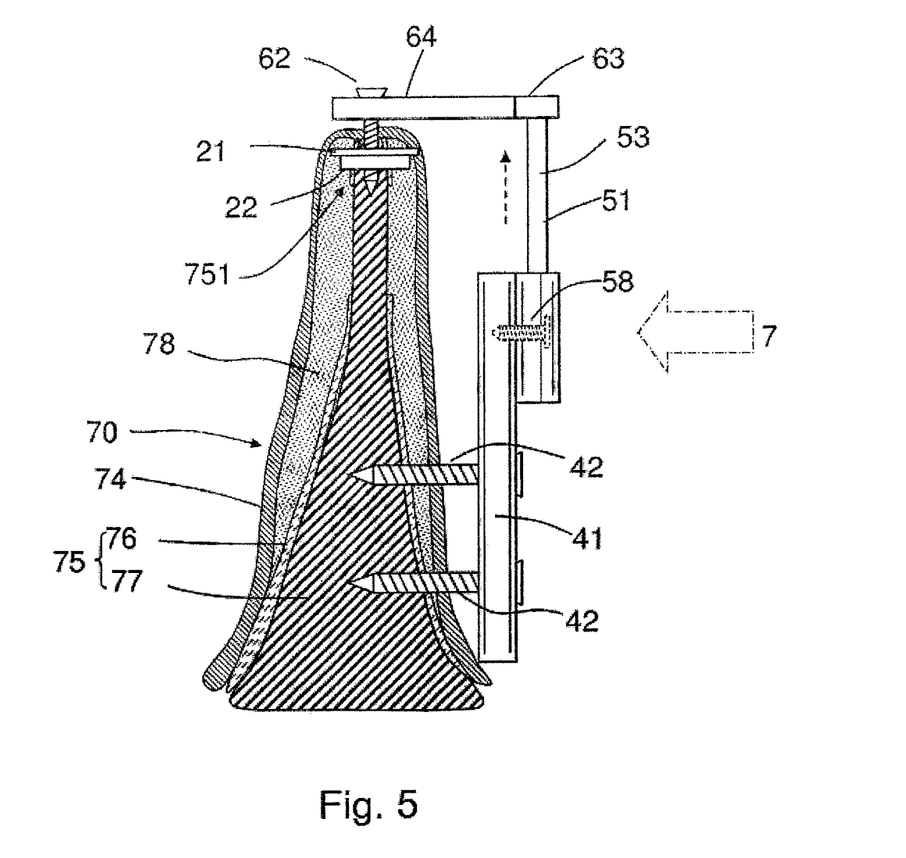
FIG. 5 is a cross-sectional view of the alveolar bone vertically augmented by the alveolar bone augmentation kit shown in FIG. 3.

Referring to FIG. 5, the vertical augmentation of the alveolar bone 75 by the alveolar bone augmentation kit 10 will be described. The vertical augmentation set 30 is used to execute the vertical augmentation during the lateral augmentation by the lateral augmentation set 20. To this end, the elevating rod 52 is rotated relative to the beam 51 so that the former is lifted from the latter. Hence, the plate 61 and the fastener 62 are lifted, and so is the lateral augmentation set 20 connected to the fastener 62. Accordingly, the distracted bone fragment 751 is lifted, and the new bone 78 grows upward and fills the space defined between the gingiva 74 and the alveolar bone 75. The lift of the distracted bone fragment 751 can be a step-by-step process or a one-step process.

As mentioned above, the distracted bone fragment 751 is formed via the bone decortication or the corticotomy. Based on clinical observation, the bone decortication or corticotomy expedites the growth and lengthening of the alveolar bone 75. This is because a fracture or injury of bone cortex will accelerate growth and repair mechanism of the surrounding soft and hard tissue. This phenomenon is called "regional acceleratory phenomenon" ("RAP"). When the vertical augmentation set 30 lifts the distracted bone fragment 751, the RAP takes place so that the bone repair near the cut in the cortex 76 is expedited. However, during the repair, the distracted bone segment 751 is further distracted and separated. The vertical dimension of the alveolar bone 75 is increased due to the repetition of the process of distraction and repair. The nearby soft tissues also grow in the same dimension following the distraction. Hence, the augmentation of the alveolar bone 75 by the alveolar bone augmentation kit 10 based on the bone decortication or corticotomy is effective and efficient.

Figure 6:
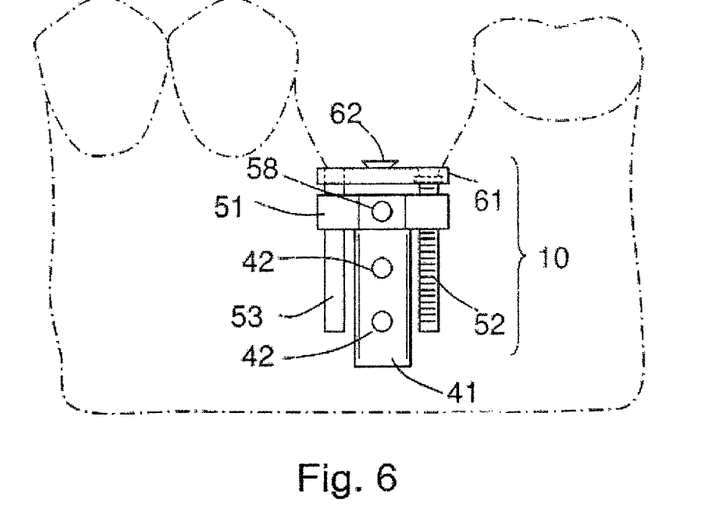
FIG. 6 is a side view of the alveolar bone and the alveolar bone augmentation kit shown in FIG. 3.
Figure 7:
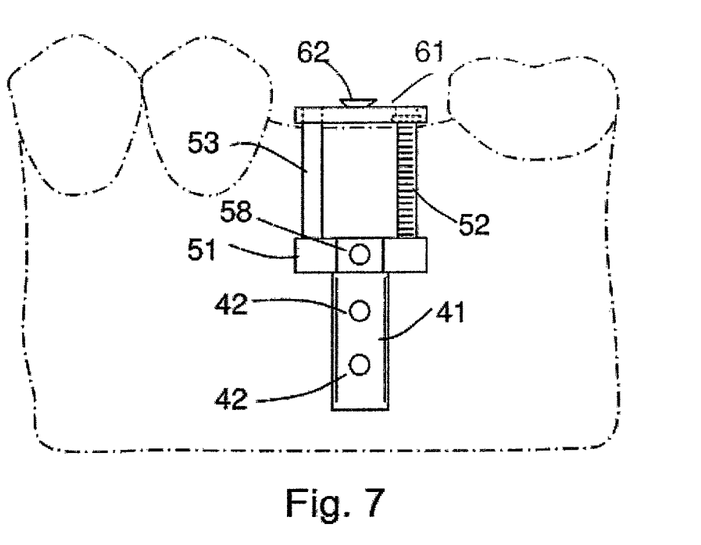
FIG. 7 is a side view of the alveolar bone and the alveolar bone augmentation kit shown in FIG. 5.

The alveolar bone augmentation kit 10 is used to change the alveolar bone 75 into an augmented state shown in FIG. 7 from an atrophic state shown in FIG. 6. In the augmented state, the alveolar bone 75 exhibits an adequate height and width. It should be noted that the lateral augmentation set 20 and the vertical augmentation set 30 can be used independent of each other.

The present invention has been described via the detailed illustration of the preferred embodiment. Those skilled in the art can derive variations from the preferred embodiment without departing from the scope of the present invention. Therefore, the preferred embodiment shall not limit the scope of the present invention defined in the claims.

The invention claimed is:

1. An alveolar bone augmentation kit including:
a lateral augmentation set made of at least one bone graft material and made with an aperture, wherein the lateral augmentation set can be implanted in an alveolar bone;
a vertical augmentation set including:
a first attachment unit including a post and a fastener for securing the post to a side of the alveolar bone;
an adjustment and lift unit including a beam, an elevating rod movably connected to the beam, and a joint for rotationally connecting the beam to a side of the post; and
a second attachment unit including a plate with a first portion placed against the elevating rod and a second portion with an opening defined therein and a fastener adapted to be driven in a distracted bone fragment via the aperture of the lateral augmentation set and the opening of the second portion of the plate.

2. The alveolar bone augmentation kit according to claim 1, wherein the lateral augmentation set includes a first ringer and a second ring coaxially connected to the first ring.

3. The alveolar bone augmentation kit according to claim 2, wherein the first ring is made with an external diameter longer than that of the second ring.

4. The alveolar bone augmentation kit according to claim 2, wherein the first ring is made of at least one material selected from the group consisting of a tissue membrane, a collagen membrane and a polytetrafluoroethylene membrane, wherein the second ring is made of at least one material selected from the group consisting of an osteo-conductive material and an osteo-inductive bone graft material.

5. The alveolar bone augmentation kit according to claim 1, wherein the joint includes a first contact face formed on the post, a second contact face formed on the beam for rotational contact with the first contact face, and a fastener centrally inserted in the first and second contact faces.

6. The alveolar bone augmentation kit according to claim 5, wherein the first contact face includes angle-retaining elements formed thereon, wherein the second contact face includes angle-retaining elements for engagement with the angle-retaining elements of the first contact face.

7. The alveolar bone augmentation kit according to claim 6, wherein each of the angle-retaining elements of the first contact face is a boss, wherein each of the angle-retaining elements of the second contact face is a recess for receiving a respective one of the bosses.

8. The alveolar bone augmentation kit according to claim 6, wherein each of the angle-retaining elements of the first contact face is a recess, wherein each of the angle-retaining elements of the second contact face is a boss for insertion in a respective one of the recesses.

9. The alveolar bone augmentation kit according to claim 1, wherein the adjustment and lift unit further includes a guiding rod secured to the first portion of the plate and movably inserted through the beam, wherein the guiding rod is parallel to the elevating rod.

10. The alveolar bone augmentation kit according to claim 1, wherein the beam includes a screw hole defined therein, wherein the elevating rod is a threaded bolt driven in the screw hole.

11. An alveolar bone augmentation kit including a lateral augmentation set 20 and a vertical augmentation set including:
a first attachment unit including a post and a fastener for securing the post to a side of the alveolar bone;
an adjustment and lift unit including a beam, an elevating rod movably connected to the beam, and a joint for rotationally connecting the beam to a side of the post; and
a second attachment unit including a plate formed with a first portion placed against the elevating rod and a second portion with an opening defined therein and a fastener adapted to be driven in an upper portion of the alveolar bone via a aperture of the lateral augmentation set and the opening of the second portion of the plate.

12. The alveolar bone augmentation kit according to claim 11, wherein the joint includes a first contact face formed on the post, a second contact face formed on the beam for rotational contact with the first contact face, and a fastener centrally inserted in the first and second contact faces.

13. The alveolar bone augmentation kit according to claim 12, wherein the first contact face includes angle-retaining elements formed thereon, wherein the second contact face includes angle-retaining elements for engagement with the angle-retaining elements of the first contact face.

14. The alveolar bone augmentation kit according to claim 13, wherein each of the angle-retaining elements of the first contact face is a boss, wherein each of the angle-retaining elements of the second contact face is a recess for receiving a respective one of the bosses.

15. The alveolar bone augmentation kit according to claim 13, wherein each of the angle-retaining elements of the first contact face is a recess, wherein each of the angle-retaining elements of the second contact face is a boss for insertion in a respective one of the recesses.

16. The alveolar bone augmentation kit according to claim 11, wherein the adjustment and lift unit further includes a guiding rod secured to the first portion of the plate and movably inserted through the beam, wherein the guiding rod is parallel to the elevating rod.

17. The alveolar bone augmentation kit according to claim 11, wherein the beam includes a screw hole defined therein, wherein the elevating rod is a threaded bolt driven in the screw hole.

* * * * *